United States Patent [19]

Maurer et al.

[11] 4,431,002
[45] Feb. 14, 1984

[54] MODULATED DEEP AFFERENT STIMULATOR

[75] Inventors: Donald D. Maurer; David E. Swift, both of Anoka; Zosim Ioffe, St. Paul, all of Minn.

[73] Assignee: EMPI Inc., Fridley, Minn.

[21] Appl. No.: 271,258

[22] Filed: Jun. 8, 1981

[51] Int. Cl.³ .............................................. A61N 1/36
[52] U.S. Cl. ................................................... 128/422
[58] Field of Search ............ 128/419 P, 419 E, 419 F, 128/419 PG, 421, 422, 423, 795, 796, 1 B

[56] References Cited

U.S. PATENT DOCUMENTS

| | | | |
|---|---|---|---|
| 2,808,826 | 10/1957 | Reiner et al. | 128/2.1 |
| 3,204,124 | 8/1965 | Durio, Jr. | 307/265 |
| 3,318,158 | 5/1967 | Bromander et al. | 328/173 |
| 3,646,940 | 3/1972 | Timm et al. | 128/421 |
| 3,817,254 | 6/1974 | Maurer | 128/421 |
| 3,888,261 | 6/1975 | Maurer | 128/421 |
| 3,897,787 | 8/1975 | Blanchard | 128/422 |
| 3,902,502 | 9/1975 | Liss et al. | 128/422 |
| 3,908,669 | 9/1975 | Man et al. | 128/422 |
| 4,014,347 | 3/1977 | Halleck et al. | 128/422 |
| 4,121,594 | 10/1968 | Miller et al. | 128/422 |
| 4,210,151 | 7/1980 | Keller, Jr. | 128/421 |
| 4,211,230 | 7/1980 | Woltosz | 128/421 |
| 4,293,817 | 10/1981 | DeMichele | 307/264 |
| 4,324,253 | 4/1982 | Greene et al. | 128/421 |

Primary Examiner—William E. Kamm
Assistant Examiner—Mitchell J. Shein
Attorney, Agent, or Firm—Burd, Bartz & Gutenkauf

[57] ABSTRACT

A transcutaneous electrical nerve stimulation apparatus having stimulus electrical pulses modulated in time and intensity to stimulate afferent and efferent nerves and cause the release of endogenous opiates which suppress pain. An astable pulse generator provides a first train of pulses at a selected repetition rate. A monostable pulse generator connected to receive the first train of pulses supplies a second pulse train having the frequency of the first train. The width of the pulses of the first train is varied over a predetermined range. A second monostable pulse generator connected to pulse amplifiers receives the first and second train of pulses and provides a supply pulse to the patient. Adjustable pulse modulators connected to the second pulse generators function to simultaneously increase the repetition rate of the first train of pulses and decrease the amplitude and pulse width of the second train of pulses, the change being between two predetermined levels for all three parameters with the magnitude of change, i.e. the percent of modulation being determined by the setting of the patient rate, and pulse width control.

8 Claims, 4 Drawing Figures

MODULATED DEEP AFFERENT STIMULATOR

TECHNICAL FIELD

This invention relates to the field of medical electronics, and more particularly to apparatus for treating patient pain by application of electrical stimuli to the body surface of the patient.

BACKGROUND OF THE INVENTION

It is well known that pain can be alleviated by electrical pulses applied to the surface of the body or to electrodes implanted within the body. Initially, this electrical stimulation was applied in such a manner that the energy was only sufficient to stimulate superficial sensory nerves, and effort was made to avoid stimulating deep sensory and muscle nerves which produce fasciculations (twitch contractions). Subsequently it was found that electrical stimulation at sufficiently high levels to elicit muscle contractions resulted in greatly improved long term analgesia, with substantial pain relief carry-over after ceasing stimulation, but pain patients were in general unable to tolerate the unpleasant sensations which accompanied the high intensity stimulation.

To avoid this it has been proposed to stimulate muscle and deep sensory nerves with short trains of electrical pulses, the pulse trains being at a low frequency. By this procedure, the current can be increased by one-third to one-half obtaining the necessary contraction intensity level without the painful response from the stimulus. Conventional transcutaneous electric nerve stimulation usually consists of a continuous train of pulses with three variable parameters. The rate may vary between 1 to 100 pulses per second, output between 0 to 70 milliamperes peak-to-peak, and pulse width between 0 to 400 micro-seconds. High rate transcutaneous electrical nerve stimulation usually refers to rates greater than 50 pulses per second. At these higher rates, if the intensity is increased to a level which produces muscle contractions, few patients can tolerate the resulting painful stimulus sensations. By interrupting the pulse train periodically at a low rate, that is, by cycling the stimulation on and off, the sensations can be reduced to a degree, but generally patients cannot tolerate even interrupted pulses at the level necessary for muscle stimulation due to adverse reaction to the low rate of interruption of the current often referred to as "Chinese water torture sensation". By "modulating", that is by varying automatically the stimulus parameters in a prescribed manner, one produces a new sensation that is different than any one setting of parameters. The particular manner of automatic variation is important, that is whether rate is varied alone, amplitude alone, pulse width alone, or in various combinations. In addition, it is of vital importance to provide a means for the patient to adjust individual parameters of the stimulus manually during the modulation so as to achieve a base range of parameters that they perceive as more pleasant than others. No single combination of parameters is optimum for the patient, rather it is the variations around base parameters that is important, and the patient must determine this setting while the stimulator is modulated.

In addition, an automatic means must be provided such that the percent of modulation increases with increases in the manual setting of parameters by the patient, as high rates, wide pulses and higher intensity mask the changes caused by modulation, there the change must be larger. Also, at low levels of intensity for a sensitive patient the percent change must be smaller in order to prevent startling or causing painful sensation.

SUMMARY OF THE INVENTION

The present invention comprises transcutaneous electrical nerve stimulation apparatus in which the stimulus pulses are modulated in both time and intensity in a prescribed manner, the pulse amplitude and width decreasing, while the pulse repetition rate increases, and vice versa. The result of this complex variation in the electrical stimulus is to produce a comfortable and pleasant sensation at levels sufficient to produce muscle contractions and stimulation of deep afferent nerves and so cause the release of endogenous opiates, such as endorphin, which suppress pain.

Various advantages and features of novelty which characterize the inventive are pointed out with particularity in the claims annexed hereto and forming a part hereof. However, for a better understanding of the invention, its advantages, and objects obtained by its use, reference should be had to the drawing which forms a further part hereof, and to the accompanying descriptive matter, in which there is illustrated and described a preferred embodiment of the invention.

BRIEF DESCRIPTION OF THE DRAWINGS

In the drawings, in which like reference numerals indicate corresponding parts throughout the several views.

DESCRIPTION OF THE PREFERRED EMBODIMENT

Figure 1:
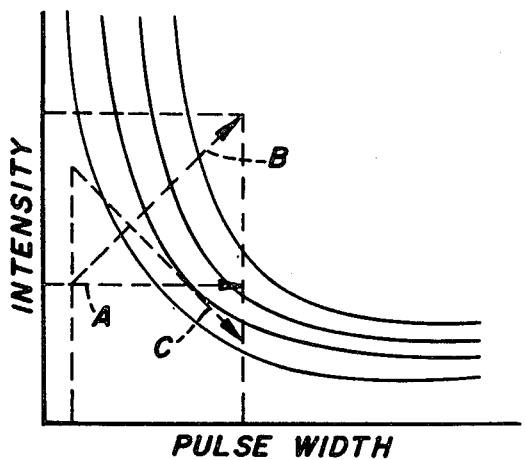
FIG. 1 is a diagram of strength-duration curves for various classes of nerve fibers.

FIG. 1 is a diagram of how strength-duration curves would appear for a different class of nerves if all were plotted on the same coordinates. Here stimulus intensity increases along the vertical axis and pulse width increases along the horizontal axis. Curve A shows the path of modulation in which the pulse width is varied, the amplitude remaining constant. Curve B shows the path of modulation in which amplitude increases with pulse width, and has been preferred modulation to maximize the recruitment with time of various classes of nerves, thereby increasing sensory input to the biological system. Curve C shows the path of modulation in which amplitude decreases with pulse width.

Figure 2:
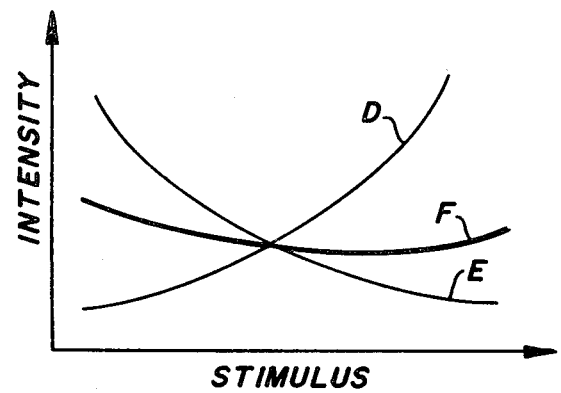
FIG. 2 shows the relation between the pulse modulations of FIG. 1 and the subjective perception of intensity by the patient.

Turning now to FIG. 2, the curves are plotted which show the variation of the perception or subjective awareness of stimulation intensity on the vertical axis with rate decrease and pulse amplitude and pulse width on the horizontal axis increase. Curve D corresponds to Curve B of FIG. 1, and shows that as the pulse amplitude and pulse width increase, the intensity perceived by the patient also increases. Curve E shows that if the pulse rate changes, amplitude and pulse width remaining the same, the patient perceives a decrease in stimulus intensity. Curve F shows that when the rate decreases, as intensity and pulse width increase, no great change in stimulus is sensed by the patient.

Figure 3:
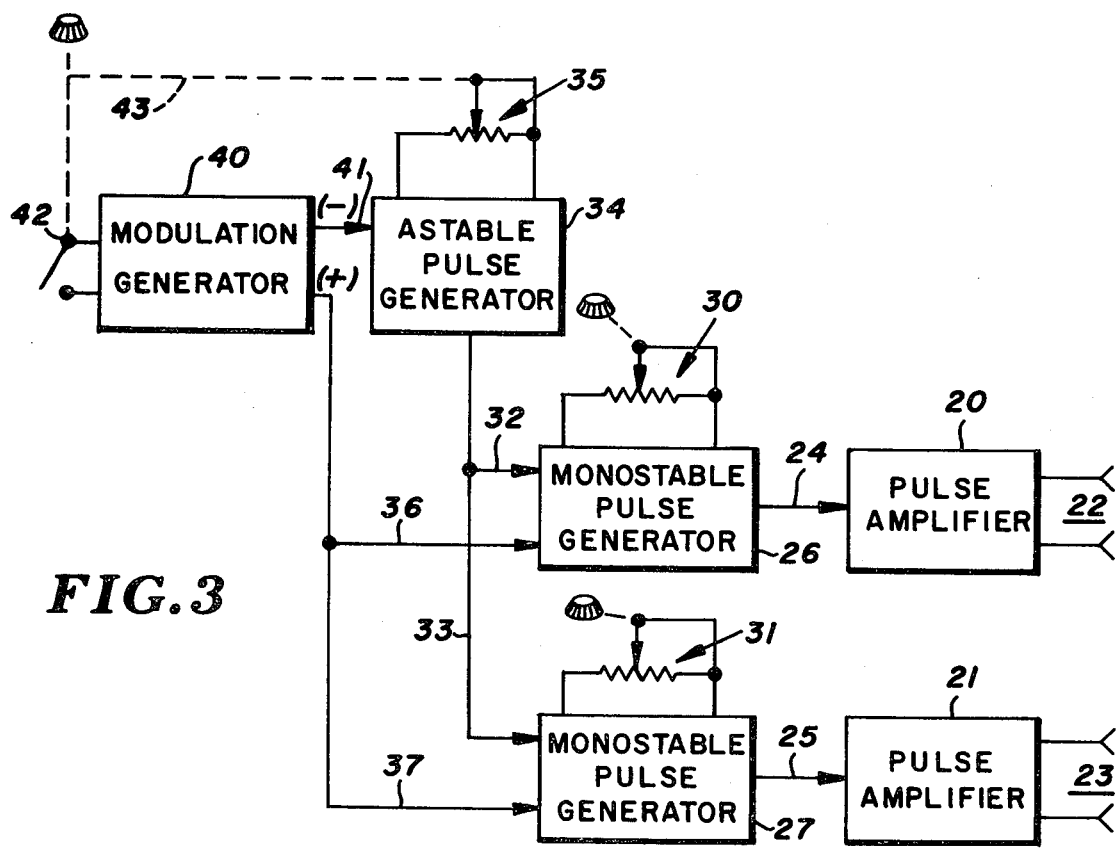
FIG. 3 is a block diagram of electrical stimulation apparatus according to the invention.

The present invention provides stimuli having variations in the pulse amplitude, pulse width, and pulse rate necessary to accomplish the result of Curve F. As shown in FIG. 3, a pair of patient treatment units 20 and 21 are shown as energizing pairs of electrodes 22 and 23. Each unit comprises a pulse amplifier and pulse-width-to-amplitude converter. The units are energized through conductors 24 and 25 from monostable pulse generators 26 and 27, respectively, having individual manual amplitude controls 30 and 31 for adjustment by the patient during modulation. Generators 26 and 27 are triggered through conductors 32 and 33 from an astable pulse generator 34 having a manual rate control 35 for adjustment by the patient. Generators 26 and 27 are controlled through conductors 36 and 37 by a modulation pulse generator and controls 40, which also control generator 34 through a conductor 41. Latching of control 40 is accomplished by a switch 42 actuated with control 35 by a mechanical connection 43.

Figure 4:
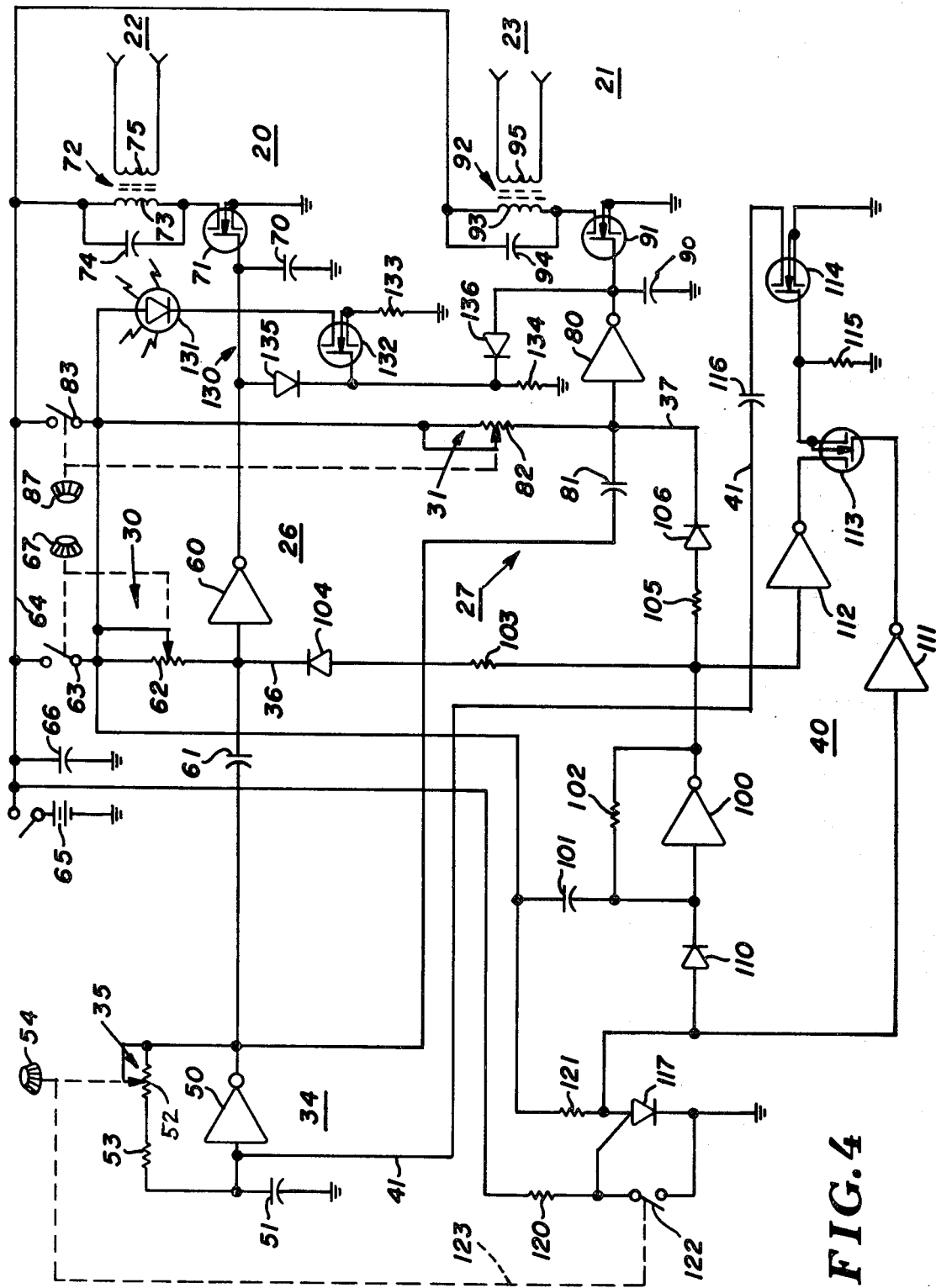
FIG. 4 is a circuit diagram of the device in FIG. 2.

Turning now to FIG. 4, astable pulse generator 34 is shown to comprise an inverter 50, a capacitor 51, and feed back resistors 52 and 53, the former being variable by an adjusting knob 54 and comprising manual adjustment 35 of FIG. 4.

Monostable pulse generator 26 is shown to comprise an inverter 60, a capacitor 61, and a variable resistor 62 connected through a switch 63 to a positive bus 64 energized from the positive terminal of a battery 65 having its negative terminal grounded. A filter capacitor 66 is provided. Switch 63 and resistor 62 are actuated by a common knob 67 and constitute adjustment 30 of FIG. 3.

Pulse amplifier 20 comprises a capacitor 70, a MOSFET (field effect transistor) 71, and a transformer 72 having a primary winding 73 shunted by a capacitor 74 and connected to bus 64, and a secondary winding 75 connected to electrodes 22.

Monostable pulse generator 27 is shown to comprise an inverter 80, a capacitor 81, and a variable resistor 82 connected through a switch 83 to positive bus 64. Switch 83 and resistor 82 are actuated by a common knob 87 and constitute adjuster 31 of FIG. 3.

Pulse amplifier 21 comprises a capacitor 90, a MOSFET 91, and a transformed 92 having a primary winding 93 shunted by a capacitor 94 and connected to bus 64, and a secondary winding 95 connected to electrodes 23.

Modulation generator 40 comprises an inverter 100, a capacitor 101 connected to bus 64 through switches 63 and 83 in parallel, and a feed back resistor 102. It is connected to generator 26 through a resistor 103, a diode 104, and conductor 36, and to generator 27 through a resistor 105, a diode 106, and conductor 37. Modulation generator 40 also comprises a diode 110, a pair of inverters 111 and 112, a pair of MOSFETS 113 and 114, a coupling resistor 115, a coupling capacitor 116, and a programmable unijunction transistor 117 powered through a pair of resistors 120 and 121. A modulation mode selector switch 122 is associated with transistor 117, and is actuated with knob 54 by a mechanical connection 123 as a part of manual adjustment 35.

A visual monitoring circuit 130 is shown to comprise a light emitting diode 131 energized from battery 65 through switches 63 and 83 in parallel under the control of a MOSFET 132 and a current limiting resistor 133. Input circuitry for MOSFET 132 has a common resistor 134 and includes a diode 135 connected to inverter 60 and a diode 136 connected to inverter 80.

In use, switch 122 is closed to inhibit modulation as will be described below, the circuit is energized to provide continuous stimulation to assist in placing one or both pairs of electrodes 22 and 23 on the patient's body in optimum positions, one or both of switches 63 and 83 being closed for this purpose, and monitoring circuit 130 giving indication of correct operation of the stimulator. After the electrodes are positioned, switch 122 is opened and the character of the stimuli is adjusted at will by operating controls 30, 31, and 35.

Inverter 50 with capacitor 51 and resistors 52 and 53 comprises astable pulse generator 34 and sets the basic pulse rate by the setting of resistor 52. The output pulses from generator 34 are supplied to capacitor 64 of monostable pulse generator 26 and capacitor 81 of monostable pulse generator 27, which supply trains of pulses to MOSFET 71 of patient unit 20 and MOSFET 91 of patient unit 21, the pulses being variable in width and amplitude in the same sense by adjusting controls 62 and 82, respectively.

Inverter 100 with capacitor 101 and resistor 102 comprises a second astable pulse generator for setting the basic rate of change of modulation for the stimulator. Transistor 117 is switched to latch in the modulation mode via diode 110, once it is selected by switch 122. When the switch is momentarily actuated, transistor 117 turns on and latches until power is removed, reverse biasing diode 110 and allowing capacitor 101 to charge. This is periodically switched by inverter 100 to produce a second train of pulses which are communicated through resistor 103 and diode 104 to inverter 60, and through resistor 105 and diode 106 to inverter 80.

When the output pulse of inverter 100 is at a high level, resistor 103 is in effect placed in parallel with resistor 62. The reduced resistance of the parallel combination causes capacitor 61 to charge more rapidly, resulting in switching of inverter 60 sooner so that the width of the pulses from inverter 60 is reduced. When the output of the inverter 100 is at a low level, diode 104 is reverse biased, since its anode is now at ground and its cathode is at supply voltage through resistor 62. This results in the output pulses of inverter 60 increasing in width to a preset value determined by the setting of resistor 62. Thus, an inverter 100 switches between high and low outputs, the pulse width alternates between wider and narrower.

This variation in pulse width is amplified by transistor 71 and transformer 72. The parameters of transformer 72 are such that as the output pulse width varies from wide to narrow, the output pulse amplitude varies from high to low, so that the stimulus to the patient fluctuates periodically in intensity and pulse width.

An action similar to that just described for inverter 60 also occurs for inverter 80 and affects the output of patient unit 21.

A second sequence of events occurs to vary the pulse rate of generator 34. When the output of inverter 100 goes to a high level, the signal is conveyed to inverter 112 whose output goes to a low level. If transistor 113 is turned on, which is the case when transistor 117 is on and a low signal is supplied to inverter 111, then the output pulse of inverter 112 can be communicated through transistor 113 to turn transistor 114 off.

When inverter 100 goes to a low level, inverter 112 has a low input and a high output. Transistor 113 is on transmitting the high level to transistor 114 to turn it on, thus connecting capacitor 116 in parallel with capacitor 51 of generator 34 and suddenly lowering the rate of pulses from inverter 50. When inverter 100 returns to a high level, capacitor 116 is disconnected from inverter 50 which resumes its former rate of pulses. As pointed out above, when the output of inverter 100 is high, the pulse width is decreased and the amplitude is reduced. This occurs simultaneously with the increase in the pulse repetition rate.

In one embodiment of the invention the output voltage was adjustable between 0 and 60 volts, the pulse width range was adjustable from 0 to 400 microseconds, the pulsing rate was adjustable from 1 to 100 pulses per second, the modulation rate was 1 cycle per second, and the changes during modulation were 0 to 40 percent amplitude, 0 to 60% pulse width, and 10 to 40% pulse rate change.

From the above it will be evident that the invention comprises a stimulator in which pulse repetition rate varies between two levels, which two levels being determined by the manual adjustment by the patient, the variation being accompanied by changes in the pulse width and amplitude, such changes being determined by the patient, so that an increase in the average pulse energy due to increase in repetition rate is counteracted by a simultaneous decrease due to individual pulses being reduced in width and amplitude.

Numerous characteristics and advantages of the invention have been set forth in the foregoing description, together with details and structure of the function of the invention, and the novel features thereof are pointed out in the appended claims. The disclosure, however, is illustrative only, and changes may be made in detail, especially in matters of shape, size, and arrangement of parts, within the principle of the invention, to the full extent indicated by the broad general meaning of the terms in which the appended claims are expressed.

The embodiments of the invention in which an exclusive property or privilege is claimed are defined as follows:

1. A medical stimulator comprising:
    astable pulse generator means for supplying a first train of electrical pulses, means operatively connected to said pulse generator means operable to adjust the pulse rate range of said electrical pulses;
    monostable pulse generator means connected to the astable pulse generator means for receiving electrical pulses therefrom, means operably connected to the monostable pulse generator means operable to adjust the width of the electrical pulses in said first train of electrical pulses over a predetermined range while simultaneously adjusting amplitude of the electrical pulses;
    means connected to said monostable pulse generator means for applying said pulses to a patient; and
    modulation means connected to the astable pulse generator means and monostable pulse generator means for causing cyclic increase and decrease in the limits of said rate range and simultaneously causing decrease and increase in said pulse rate to produce electrical pulses in said means for applying said pulses to a patient at levels sufficient to produce muscle contractions and stimulation of deep afferent nerves and cause the release of endogenous opiates to suppress pain.

2. The stimulator of claim 1 wherein: the modulation means includes first modulation means for causing cyclic alteration in the limits of said rate range; and second modulation means for causing cyclic alteration in said pulse rate between first and second values.

3. The stimulator of claim 1 wherein: the monostable pulse generator means comprise a first monostable pulse generator and a second monostable pulse generator, each generator being operably connected to the astable pulse generator and modulation means.

4. The stimulator of claim 3 wherein: each monostable pulse generator includes means to adjust the width of the electrical pulses in the first train of pulses over a predetermined range while simultaneously adjusting the amplitude of said electrical pulses.

5. A medical stimulator comprising an astable pulse generator providing a first train of pulses at a repetition rate determined by a characteristic of said generator means operatively connected to said pulse generator operable to adjust the pulse rate range of said electrical pulses; a first monostable pulse generator connected to the astable pulse generator to receive the pulses of said first train and supply a second pulse train having the frequency of said first train, means operably connected to the monostable pulse generator operable to adjust the width of said first train of electrical pulses over a predetermined range while simultaneously adjusting amplitude of the electrical pulses; means connected to the first monostable pulse generator for supplying pulses from said train to a patient; a second monostable pulse generator connected to the astable pulse generator to receive the pulses of said first train and supply a third train of pulses having the frequency of the first train, means operably connected to the second monostable pulse generator operable to adjust the width of the electrical pulses in said first train of electrical pulses over a predetermined range and while simultaneously adjusting amplitude of the electrical pulses, means connected to the second monostable pulse generator for supplying pulses from said third train to a patient; and modulation means connected to said astable pulse generator for causing cyclic increase and decrease in the limits of said rate range and simultaneously causing decrease and increase in said pulse rate to produce electrical pulses in said means for applying said pulses to a patient at levels sufficient to produce muscle contractions and stimulation of deep afferent nerves and cause the release of endogenous opiates to suppress pain.

6. A stimulator according to claim 5 including means for visually observing the presence of said second pulse train.

7. The stimulator of claim 6 wherein: the means for modulating the pulses supplied to the patient comprise modulation generator means connected to the first astable pulse generator and monostable pulse generator.

8. The stimulator of claim 5 wherein: the modulation means includes first modulation means for causing cyclic alteration in the limits of said first range, and second modulation means for causing cyclic alteration in said pulse rate between the first and second values.

* * * * *

UNITED STATES PATENT AND TRADEMARK OFFICE
CERTIFICATE OF CORRECTION

PATENT NO. : 4,431,002
DATED : February 14, 1984
INVENTOR(S) : Donald D. Maurer et al It is certified that error appears in the above-identified patent and that said Letters Patent are hereby corrected as shown below:

Column 2, line 18, "inventive" should be -- invention --.

Column 4, line 16, "64" should be -- 61 --.

Column 4, line 46, "an" should be -- as --.

Signed and Sealed this

Twenty-fifth Day of September 1984

[SEAL]

Attest:

GERALD J. MOSSINGHOFF

Attesting Officer    Commissioner of Patents and Trademarks